United States Patent
Dale

(10) Patent No.: US 10,441,274 B2
(45) Date of Patent: Oct. 15, 2019

(54) SUTURE CLIPS AND METHODS OF DEPLOYING SAME

(71) Applicant: St. Jude Medical, Cardiology Division, Inc., St. Paul, MN (US)

(72) Inventor: Theodore Paul Dale, Corcoran, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 153 days.

(21) Appl. No.: 15/401,391

(22) Filed: Jan. 9, 2017

(65) Prior Publication Data

US 2017/0196553 A1     Jul. 13, 2017

Related U.S. Application Data

(60) Provisional application No. 62/278,033, filed on Jan. 13, 2016.

(51) Int. Cl.
    *A61B 17/04*     (2006.01)
(52) U.S. Cl.
    CPC .. *A61B 17/0487* (2013.01); *A61B 2017/0454* (2013.01); *A61B 2017/0488* (2013.01)

(58) Field of Classification Search
    CPC ............ A61B 17/0487; A61B 17/0401; A61B 2017/0454; A61B 2017/00867; A61B 2017/0451; A61B 2017/0488
    See application file for complete search history.

(56) References Cited

U.S. PATENT DOCUMENTS

| | | | |
|---|---|---|---|
| 2004/0260317 A1* | 12/2004 | Bloom | A61F 2/2487 606/151 |
| 2007/0179530 A1* | 8/2007 | Tieu | A61B 17/0487 606/232 |
| 2012/0283749 A1 | 11/2012 | Sauer | |
| 2013/0110230 A1* | 5/2013 | Solem | A61F 2/2457 623/2.38 |

\* cited by examiner

*Primary Examiner* — Diane D Yabut
*Assistant Examiner* — Majid Jamialahmadi
(74) *Attorney, Agent, or Firm* — Lerner, David, Littenberg, Krumholz & Mentlik, LLP

(57) ABSTRACT

A suture clip includes a body having a proximal end, a distal end, and a sidewall defining a lumen through the body from the proximal end to the distal end. At least one engaging arm is movable between a loaded condition in which the engaging arm is oriented substantially parallel with the sidewall of the body, and a relaxed condition in which the engaging arm is oriented transversely to the sidewall of the body and at least partially disposed within the lumen.

12 Claims, 9 Drawing Sheets

SUTURE CLIPS AND METHODS OF DEPLOYING SAME

CROSS-REFERENCE TO RELATED APPLICATIONS

The present application claims the benefit of the filing date of U.S. Provisional Patent Application No. 62/278,033 filed Jan. 13, 2016, the disclosure of which is hereby incorporated herein by reference.

BACKGROUND OF THE INVENTION

The present invention relates to surgical methods using sutures. More particularly, the present invention relates to the use of clips as an alternative to suture knots in practicing such surgical methods.

Sutures are used during medical procedures to couple components of a medical device to each other or to body tissue, or to close openings. After passing the suture through the desired path, the surgeon typically forms a knot by manually tying together a pair of suture tails. Automatic suture tying systems are also being developed.

There are a number of disadvantages of knotting sutures together to secure tissue or components of a medical device to one another. For example, manual knot tying requires considerable dexterity, and can take considerable time. Knot tying is further complicated by the fact that surgical sutures have low friction surfaces. Therefore, it is typically necessary for a surgeon to include many "throws" when tying the knot. This multiple-throw problem occurs even if an automatic knot-tying device is used. Unfortunately, as the number of loops or "throws" incorporated into the knot increase, the knot becomes increasingly large and bulky. Moreover, the surgeon ordinarily needs to handle suture tails of adequate length prior to commencing manual knot tying. Thus, manual knot tying requires considerable space in which to both view and perform the actual suture knot tying. Therefore, knot tying is particularly difficult in areas of limited available space or access, such as, for example, in spaces within the heart. Additionally, manually tied knots often lock prior to reaching the intended amount of tension to be applied to the tissue. It would be advantageous to provide a system in which tissue may be secured with suture without the need to knot the suture tails together.

Therefore, there is a need for further improvements to the current techniques for coupling together the tails of a suture. Among other advantages, the present invention may address this need.

SUMMARY OF THE INVENTION

In some embodiments, a suture clip includes a body having a proximal end, a distal end, and a sidewall defining a lumen through the body from the proximal end to the distal end and at least one engaging arm movable between a loaded condition in which the engaging arm is oriented substantially parallel with the sidewall of the body, and a relaxed condition in which the engaging arm is oriented transversely to the sidewall of the body and at least partially disposed within the lumen.

In some embodiments, a system for deploying a suture clip at a target site, the system includes a delivery device including (i) a hollow shaft having a trailing end, a leading end, and a lumen extending therethrough from the trailing end to the leading end, (ii) a pusher slidably disposed on the hollow shaft, and (c) a sheath disposed over the hollow shaft and the pusher, and a suture clip disposed on the hollow shaft and within the sheath.

BRIEF DESCRIPTION OF THE DRAWINGS

Various embodiments of the present invention are disclosed herein with reference to the drawings, wherein.

Various embodiments of the present invention will now be described with reference to the appended drawings. It is to be appreciated that these drawings depict only some embodiments of the invention and are therefore not to be considered limiting of its scope.

DETAILED DESCRIPTION

When used in connection with devices for delivering a suture clip into a patient, the terms "trailing" and "leading" are to be taken as relative to the user of the delivery devices. "Trailing" is to be understood as relatively close to the user, and "leading" is to be understood as relatively farther away from the user. Similarly, the terms "proximal" and "distal" are to be taken as relative to a surgical site, with "proximal" being understood as relatively close to the surgical site, and "distal" being understood as relatively farther away from the surgical site.

A suture may be used to affix a medical device at a desired location. The following exemplary disclosure describes the use of one or more sutures within the heart. For example, a suture may be used to affix a heart valve, such as an aortic heart valve or mitral heart valve, within a native valve annulus. A suture may also be used to secure an annuloplasty ring at an implantation site or to pull one portion of tissue close to another portion, for example, in a heart valve leaflet repair procedure. It will be understood, however, that the disclosure is not limited to cardiac applications and that the suture clips disclosed herein may be used in any situation in which one or more sutures are to be coupled together, a suture is to be coupled to another structure, or a predetermined length of suture is to be defined.

Figure 1:
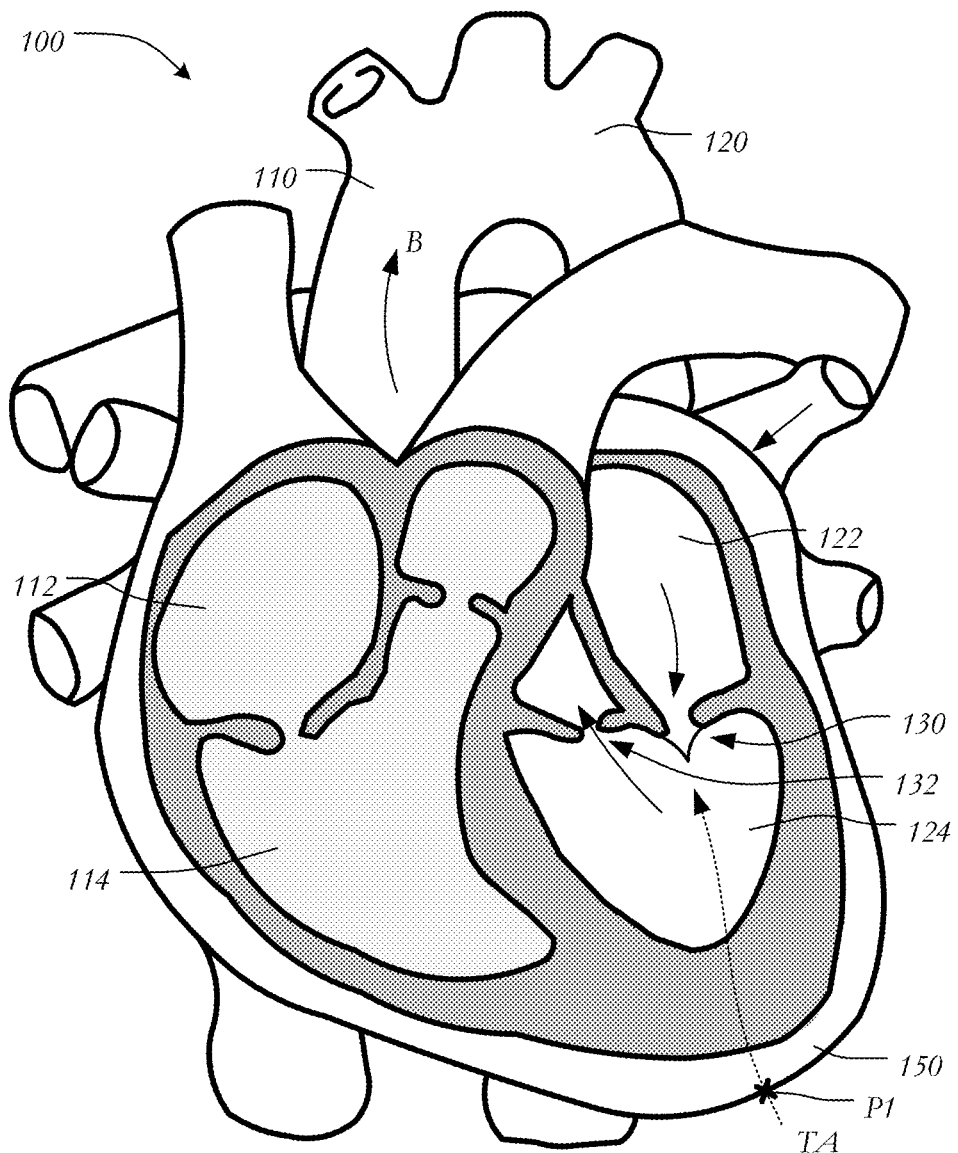
FIG. 1 is a schematic representation of a human heart showing a transapical delivery approach.

FIG. 1 is a schematic representation of a human heart 100. The human heart includes two atria and two ventricles: a right atrium 112 and a left atrium 122, and a right ventricle 114 and a left ventricle 124. Heart 100 further includes an aorta 110 and an aortic arch 120. Disposed between left atrium 122 and left ventricle 124 is mitral valve 130, and disposed between aorta 110 and left ventricle 124 is aortic valve 132. Mitral valve 130, also known as the bicuspid valve or left atrioventricular valve, is a dual-flap that opens when the pressure in left atrium 122 becomes greater than the pressure in left ventricle 124. When left ventricle 124 contracts during systole, blood flows through aortic valve 132 from the left ventricle to aorta 110. The blood flow from left atrium 122 to left ventricle 124 and then to aorta 110 is shown by arrows "B" in FIG. 1.

A dashed arrow, labeled "TA", indicates a transapical approach for repairing or replacing heart valves such as mitral valve 130 or aortic valve 132. For example, in transapical replacement of a heart valve, a small incision is made between the ribs and into the apex of left ventricle 124 at position "P1" in heart wall 150 to deliver a prosthesis or device to the target site (e.g., at a site to replace mitral valve 130). Regardless of the device being delivered or the structure being repaired, sutures are often used during the procedure and require affixation at the ends thereof.

Figure 2:
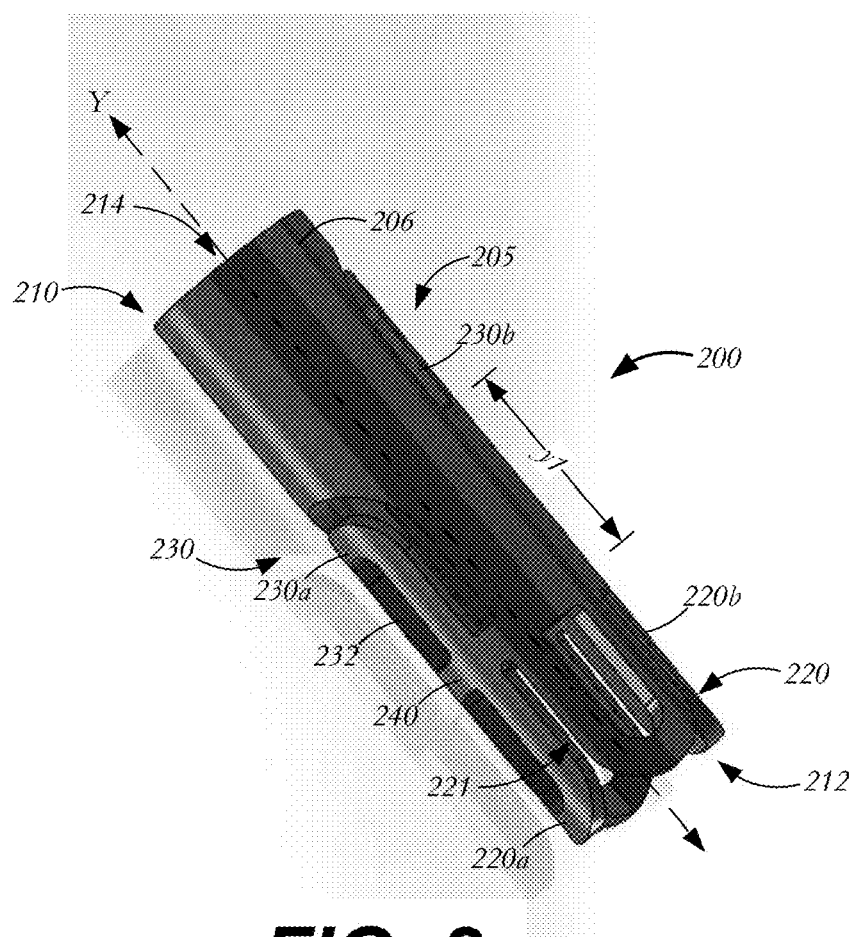
FIG. 2 is a perspective view of a suture clip in a loaded condition.

FIG. 2 is a perspective view of suture clip 200, which is capable of coupling to the tail ends of a suture. Suture clip device 200 has a generally cylindrical body 205 extending between proximal end 210 and distal end 212. Body 205 has an annular sidewall 206 defining a lumen 214 extending axially through body 205 from proximal end 210 to distal end 212 along longitudinal axis Y, lumen 214 being sized to receive one or more sutures or the tail ends of one or more sutures therethrough.

Figure 3:
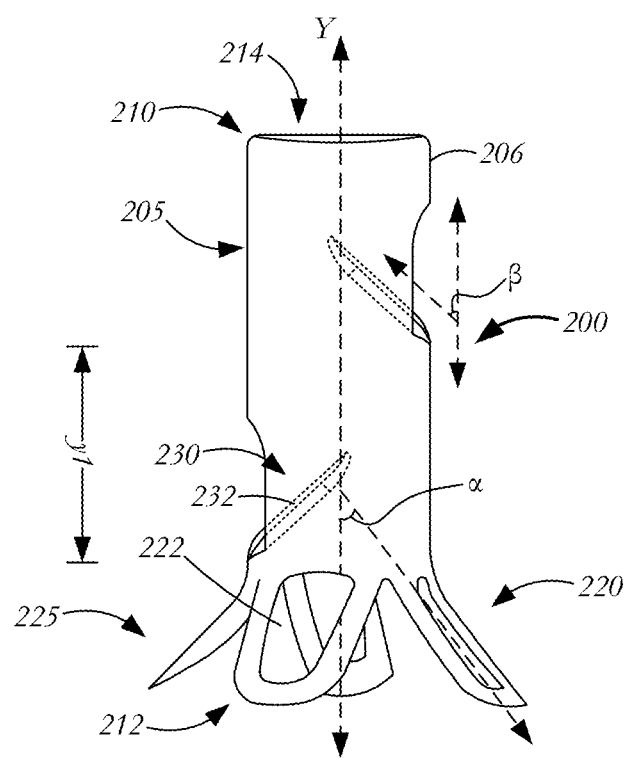
FIG. 3 is a side view of the suture clip of FIG. 2 in a relaxed condition.

While body 205 is shown as having a generally cylindrical shape, it will be understood that body 205 may be formed with other shapes such as those of a cube, a sphere, a rectangular prism, etc. Body 205 may be laser cut from a tube formed of a material that is both resilient and capable of processing to substantially preset a desired shape. Superelastic materials, bio-compatible polymers, or other materials that are capable of collapsing and expanding may also be used in forming body 205. In the embodiment depicted in FIG. 2, body 205 comprises a metal that is both resilient and capable of heat treatment to substantially set a desired preset shape (e.g., the relaxed condition after heat-setting shown in FIG. 3). FIG. 2 illustrates suture clip 200 before shape-setting, while FIG. 3 illustrates suture clip 200 in the relaxed condition after shape setting. It will be understood that suture clip 200 assumes a similar shape after heat-setting when loaded into a delivery device. Thus, the configuration shown in FIG. 2 is sometimes referred to throughout the instant description as the "loaded" condition of suture clip 200.

One class of materials which meets the aforementioned qualifications for forming body 205 is shape-memory alloys that may be heat treated to preset a desired shape, an example of which is Nitinol. Body 205 may also be formed of various materials other than Nitinol that have elastic and/or memory properties, such as spring stainless steel, trade named alloys such as Elgiloy® and Hastelloy®, CoCrNi alloys (e.g., trade name Phynox®), MP35N®, CoCrMo alloys, or a mixture of metal and polymer materials. In addition, body 250 may include a radiopaque material or other similar material to aid in ascertaining the position and/or orientation of suture clip 200 using fluoroscopy, x-rays, ultrasound or other visualization techniques.

In addition to the overall cylindrical shape of body 205 and lumen 214 defined therethrough, two other groups of features may be formed in suture clip device 200. First, a number of U-shaped lower fingers 220 may be laser cut into sidewall 206 adjacent distal end 212 so that a gap 221 is formed between adjacent fingers. As shown in FIG. 2, suture clip 200 includes four U-shaped lower fingers 220 symmetrically distributed around the circumference of distal end 212, although it will be understood that one, two, three or more than four lower fingers 220 may be formed at distal end 212 of suture clip 200. Each lower finger 220 is substantially parallel with the rest of sidewall 206 of body 205 in the loaded condition of suture clip 200 shown in FIG. 2.

A number of U-shaped engaging arms 230 likewise may be laser cut or otherwise formed in sidewall 206, the engaging arms being closer to proximal end 210 of body 205 than lower fingers 220. Optionally, the engaging arms may be aligned in the longitudinal direction with the lower fingers. Like lower fingers 220, each engaging arm 230 is substantially parallel with the rest of sidewall 206 in the loaded condition of suture clip 200. In the relaxed condition of suture clip 200, however, engaging arms 230 bend inwardly into lumen 214 of body 205, as shown in FIG. 3. In the example shown, two engaging arms 230 are cut into wall 206 on contralateral sides of body 205, the engaging arms 230 being longitudinally spaced from one another by a distance y1 defined as the longitudinal distance from the distal end of one engaging arm to the distal end of a second engaging arm. Distance y1 may be approximately ¼ to ⅓ of the full length of suture clip 200. In some variations, suture clip 200 may include only one engaging arm 230. Alternatively, suture clip 200 may include three, four or more engaging arms 230. The purpose of engaging arms 230 is to secure one or more sutures within lumen 214 of the suture clip, as will be described in more detail below.

In the example shown, the ends of the legs at the open of engaging arms 230a are connected to a transverse rib 240. Also, rib 240 is connected to the ends of the legs of the open-end of U-shaped lower fingers 220a. Rib 240 may be twisted and heat set such that lower fingers 220a and engaging arms 230a are actuated together and concurrently bend from the loaded condition to the relaxed condition and vice versa. Specifically, as a result of sharing a rib 240, any rotation of rib 240 caused by the pivoting lower finger 220a radially outward from sidewall 206 to the relaxed condition results in a concurrent pivoting of the connected engaging arm 230a into lumen 214 of body 205. It will be understood, however, that engaging arms 230 and lower fingers 220 may be spaced apart in the longitudinal direction and independently operable as is the case with engaging arm 230b and lower finger 220b.

The structure and function of lower fingers 220 and engaging arms 230 will be described in greater detail with reference to FIG. 3, which illustrates suture clip 200 in a relaxed configuration after heat-setting. As shown in FIG. 3, each of lower fingers 220 has been heat treated to return to a relaxed condition to collectively form atraumatic base 225 which contacts a surface of a medical device or body tissue without causing damage or trauma to the surface. Each lower finger 220 may have a trapezoid-shaped slot 222 to aid in the bending of the finger. In some examples, each lower finger 220 extends radially outward in the relaxed condition at an angle α with respect to longitudinal axis Y. Lower fingers 220 may be heat treated to have a relaxed condition in which they extend at an angle α of between about 0 and about 90 degrees away from the longitudinal axis Y. In at least some examples, angle α may be between about 0 and about 45 degrees.

Figure 4A:
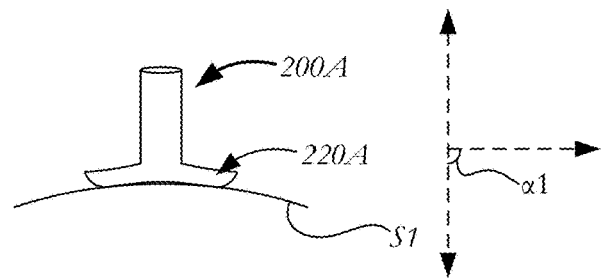
FIGS. 4A-C are schematic representations showing some possible angles of the lower fingers of the suture clip of FIG. 2.
Figure 4B:
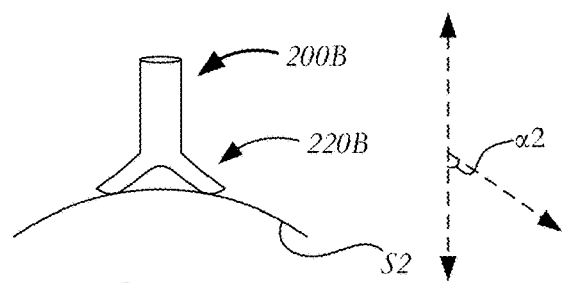
Figure 4C:
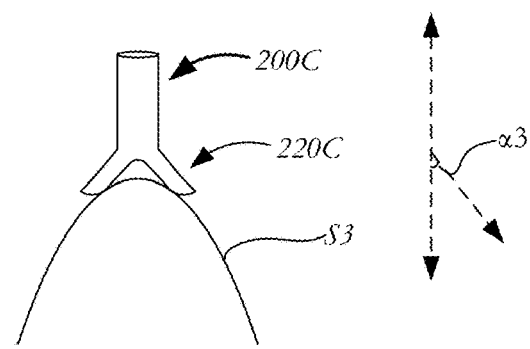

Angle α may be selected based on the desired use. For example, as shown in the schematic representations of FIGS. 4A-4C, a relatively flat surface S1 may require a suture clip 200A having lower fingers 220A disposed at a relatively large angle α1 (e.g., about 90 degrees) (FIG. 4A). This relatively large angle enables fingers 200A to contact a large area of surface S1, providing a stable interaction with the surface and spread out any forces exerted on the surface by suture clip 200A over a large area. A more curved surface S2 may require a suture clip 200B having lower fingers 220B disposed at a smaller angle α2 (e.g., about 45 degrees) (FIG. 4B), again providing a larger area of contact between fingers 200B and surface S2. A more convexly curved surface S3 may require suture clip 200C having lower fingers 220C disposed at an even smaller angle α3 (e.g., about 30 degrees) (FIG. 4C) to again maximize the area of contact between fingers 200C and surface S3. By considering the size and curvature of the surface on which a suture clip lie, lower finger arrangements may be chosen to yield improved stability of the suture clip against that surface and to spread any forces exerted by the suture clip over a larger area. While all lower fingers 220 of a given suture clip 200 have been described as having the same angle α in the relaxed condition, this is not necessarily the case. Thus, in some examples, some or all of lower fingers 220 may have angles α that are different from one another.

Returning to FIG. 3, engaging arms 230 may be heat set in a manner similar to lower fingers 220 to have a relaxed condition that is deflected radially inward toward longitudinal axis Y and disposed at least partially within lumen 214 to obstruct a portion of the lumen. Each engaging arm 230 may have a slot 232 (best seen in FIG. 2) to aid in the bending of the arm. As shown, engaging arms 230 have been deflected radially inward (e.g., to lie at least partially within lumen 214) and heat set into the relaxed condition shown. Engaging arms 230 may be deflected so as to extend at an angle β of between about 0 and about 90 degrees toward longitudinal axis Y in the relaxed condition. In at least some examples, angle β may be between about 30 and about 60 degrees. Engaging arms 230 may be bent so that its tip is very closely spaced from or contact the inner wall of body 205. Each engaging arm 230 may be deflected inwardly at the same angle. Alternatively, one engaging arm 230 may be deflected inwardly more than another.

Figure 5:
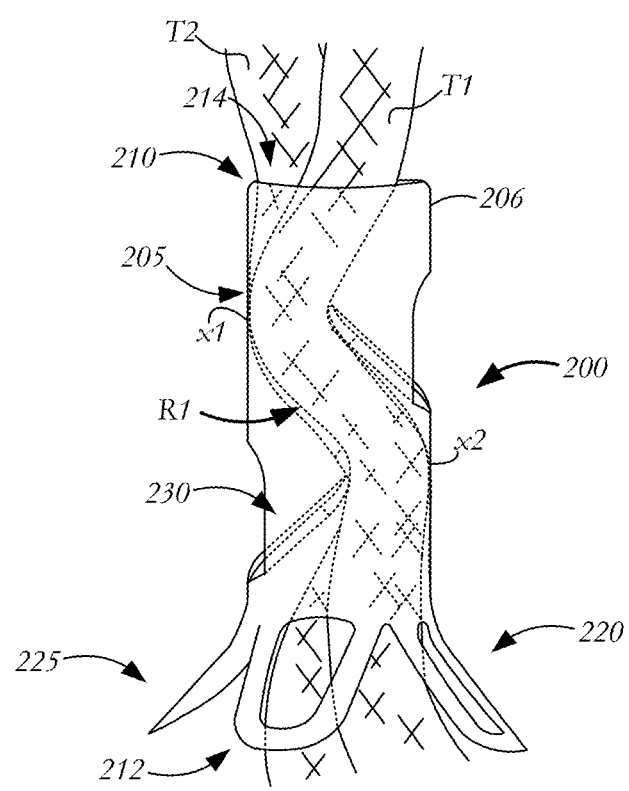
FIG. 5 is a side view of the suture clip of FIG. 2 affixing a pair of suture tails.

FIG. 5 illustrates a suture clip 200 during use. As shown, two sutures T1, T2 (or two tail ends of the same suture) pass through lumen 214 from distal end 212 to proximal end 210. Lower fingers 220 are deflected outwardly in their relaxed condition and form atraumatic base 225. Additionally, engaging arms 230 are deflected inwardly toward one another to secure sutures T1, T2 within lumen 214. Specifically, the inward deflection of engaging arms 230 creates a tortuous path R1 between the engaging arms within lumen 214. Within path R1, sutures T1, T2 may be tightly packed and secured such that frictional forces prevent sutures T1, T2 from longitudinally traveling within lumen 214. Specifically, portions of sutures T1, T2 are pressed by engaging arms 230 against inner portions of sidewall 206 at locations x1, x2 to secure the suture at these locations. Thus, sutures T1, T2 are secured and affixed at a predetermined location within lumen 214 without the need for knotting the sutures.

Figure 6:
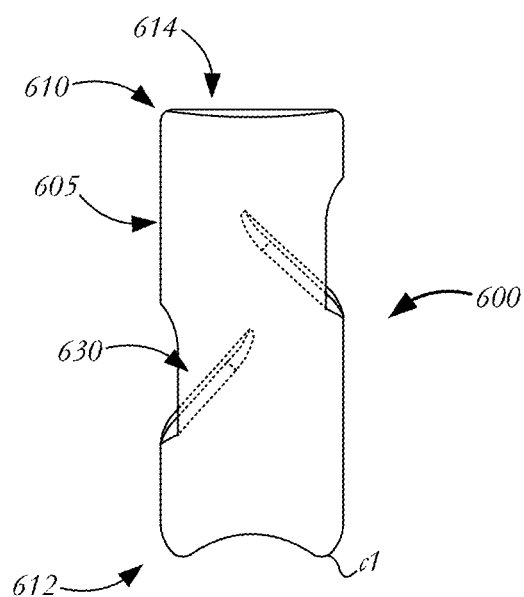
FIG. 6 is a side view of another embodiment of a suture clip having a blunted end.

In one variation, shown in FIG. 6, suture clip 600 is similar to suture clip 200 of FIG. 3 and includes a substantially cylindrical body 605 having a proximal end 610, a distal end 612, a lumen 614 extending between proximal end 610 and distal end 612, and engaging arms 630 that have been heat-set to have the relaxed condition shown. Instead of having lower fingers as described in connection with the embodiments of FIGS. 2-3, suture clip 600 is atraumaticly blunted at distal end 612, the blunted distal end having curved portions c1 with no sharp edges so as to reduce the likelihood of piercing or damaging a medical device or body tissue. It will be appreciated that blunted end 612 has a fixed shape and is not movable between relaxed and loaded conditions.

Figure 7:
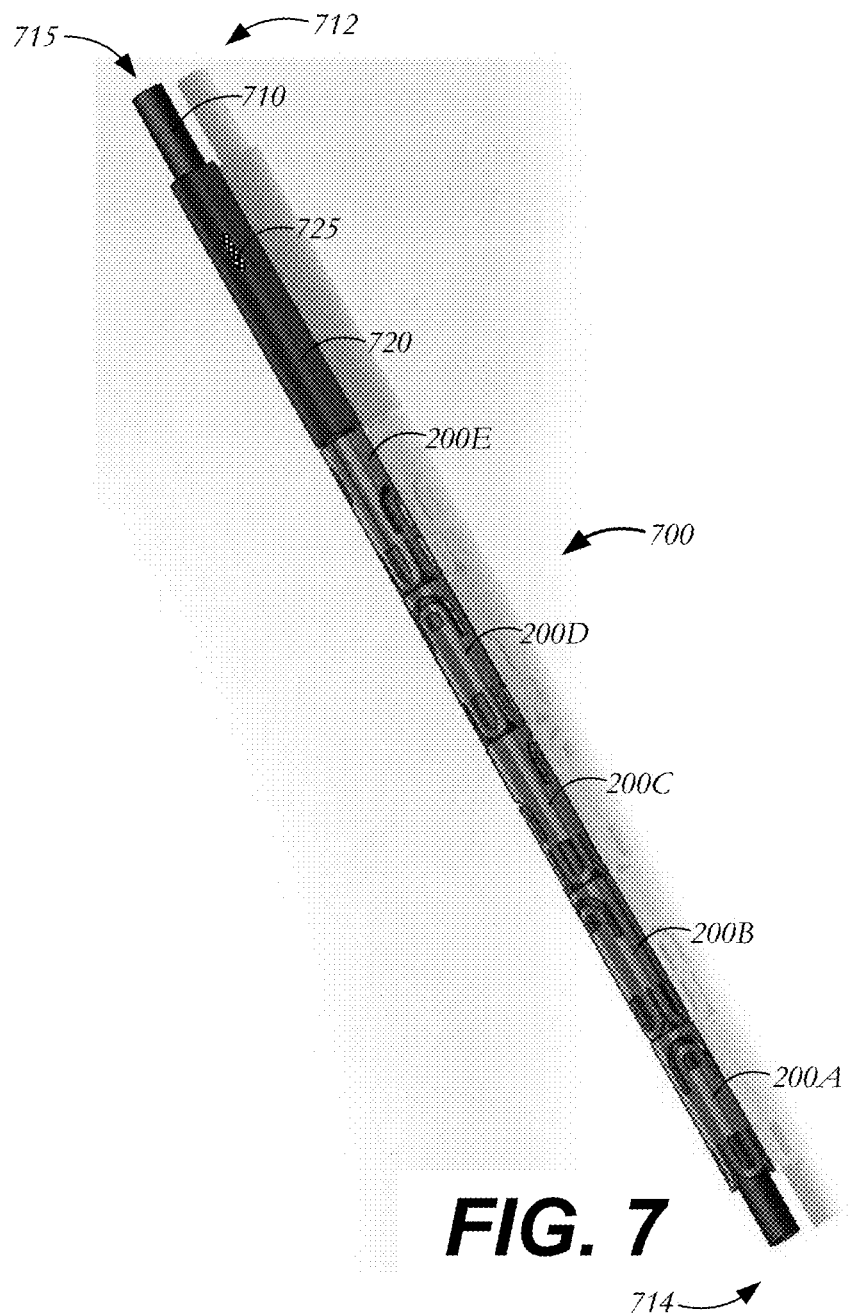
FIG. 7 is partial side view of a delivery device for deploying suture clips.
Figure 8:
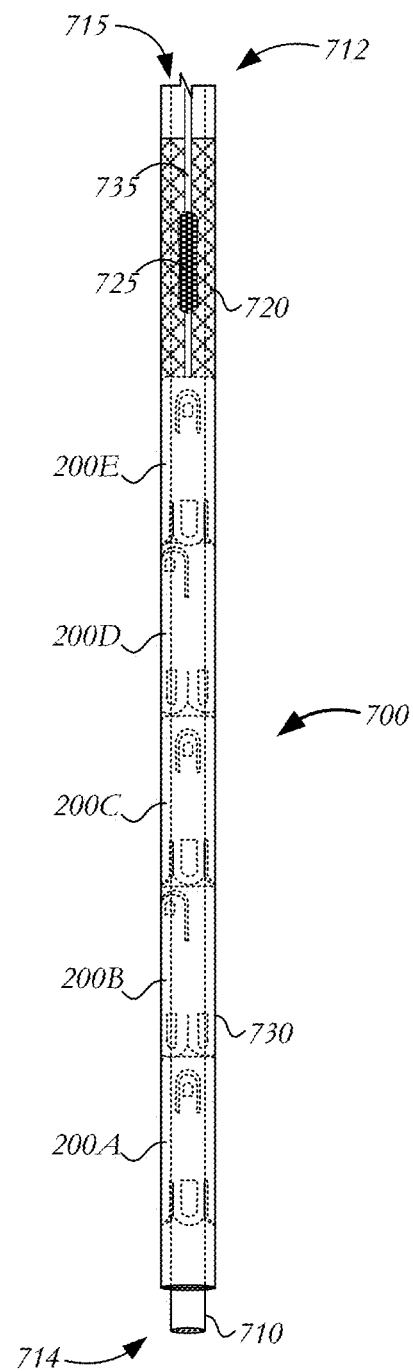
FIG. 8 is a partial side view of the delivery device of FIG. 7, showing the suture clips in the interior thereof.

FIGS. 7-8 illustrate one possible method for delivering suture clips 200 or 600 to a surgical site and a delivery device for use in conjunction therewith. Delivery device 700 may be used to deliver one or more suture clips, such as suture clips 200A-E. Delivery device 700 includes a hollow shaft 710 having a trailing end 712, a leading end 714, and an outer diameter less than the inner diameter of each suture clip. Hollow shaft 710 and suture clips 200A-E may be sized so that the hollow shaft is insertable through the lumen 214 of each suture clip as the suture clips slide onto the hollow shaft. A lumen 715 extending through hollow shaft 710 from trailing end 712 to leading end 714 may be sized to receive one or more sutures (not shown).

Delivery device 700 further includes a pusher 720 slidably disposed over hollow shaft 710. Pusher 720 may have an outer diameter that is approximately equal to, or slightly larger than, the diameter of each suture clip 200A-E in the loaded condition. Pusher 720 may be outfitted with an actuator 725 to aid in the translation of the pusher along hollow shaft 710. In one example, actuator 725 is a button protruding radially outward from pusher 720. As explained below, the translation of pusher 720 along hollow shaft 710 may deploy suture clips 200A-E from delivery device 700.

An outer sheath 730 (shown in FIG. 8) may be disposed over hollow shaft 710, suture clips 200A-E and pusher 720. Outer sheath 730 and hollow shaft 710 may both be coupled to a handle (not shown) at their trailing ends. Outer sheath 730 is preferably sized to keep lower fingers 220 of suture clips 200A-E from extending radially outward to their relaxed condition until a suture clip is deployed from the delivery device. Outer sheath 730 may include a longitudinally extending slot 735 through which actuator 725 protrudes for operation by a user. Thus, pushing actuator 725 toward the leading end 714 or trailing end 712 of hollow shaft 710 results in a concurrent movement of pusher 720 without interference from outer sheath 730.

In use, suture clips 200A-E may be loaded onto hollow shaft 710 and covered with outer sheath 730 such that the clips are disposed in their loaded condition, the clips being sandwiched between hollow shaft 710 and outer sheath 730. One or more sutures may then be used in a medical procedure, such as heart valve repair or replacement. Once the procedure has been completed and the sutures are in position to be secured, the one or more sutures may be threaded through lumen 715 of hollow shaft 710 from leading end 714 to trailing end 712. Actuator 725 may then be advanced through slot 735 to slide pusher 720 forward toward leading end 714 of hollow shaft 710.

By sliding pusher 720 along hollow shaft 710 toward the leading end 714 thereof, each of suture clips 200A-E may be selectively and serially deployed from delivery device 700. That is, as pusher 720 is advanced toward the leading end 714 of hollow shaft 710, the pusher exerts a force against the adjacent suture clip 200E, causing it to advance toward leading end 714. This movement is transmitted to each successive suture clip in the series of suture clips on hollow shaft 710 until the first suture clip 200A is pushed off the hollow shaft. Thus, movement of pusher 720 will force suture clip 200A out of outer sheath 730 and off of hollow shaft 710 onto the sutures that were threaded through lumen 715. As suture clip 200A is deployed, the absence of hollow shaft 710 from lumen 714 of clip 200A enables engaging arms 230 to return to their relaxed condition and the absence of outer sheath 730 from around clip 200A enables lower fingers 220 to return to their relaxed condition. In other words, deployment of suture clip 200A will cause lower fingers 220 to expand radially outward and engaging arms 230 to deflect radially inward to latch onto the sutures and press them against the inner sidewalls of the suture clips, the sutures becoming affixed within lumen 214 of the suture clip as shown in FIG. 5. With suture clip 200A secured in place, the surgeon or operator may cut the suture above proximal end 210 of the suture clip, leaving the suture clip in place to secure the suture at the target site.

Figure 9:
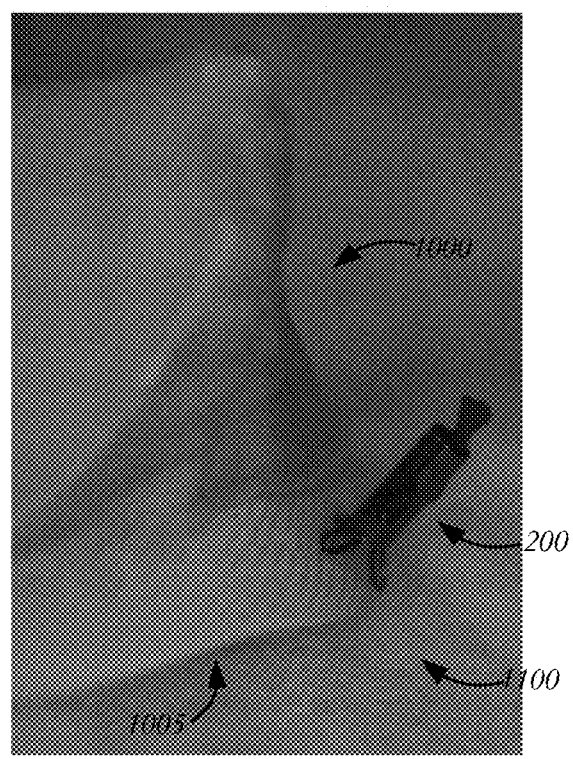
FIG. 9 is a schematic representation of a suture clip coupled to a prosthetic aortic valve.

FIG. 9 illustrates an exemplary use of a suture clip 200 to affix a suture coupling cuff 1005 of prosthetic aortic valve 1000 to body tissue 1100. The coupling of aortic valve 1000 to tissue 1100 may require multiple suture clips. Accordingly, additional suture clips 200B-200E may be deployed at the same or different locations around the cuff 1005.

It will be appreciated that the various dependent claims and the features set forth therein can be combined in different ways than presented herein. For example, a delivery device may be capable of housing more or fewer suture clips than described. Instead of securing one suture or only two tail ends of one or more sutures, each suture clip may be capable of securing three, four or more sutures. Additionally, it will be understood that multiple delivery devices may be employed to deliver suture clips. It will also be appreciated that any of the features described in connection with individual embodiments may be shared with others of the described embodiments.

In some embodiments, a suture clip includes a body having a proximal end, a distal end, and a sidewall defining a lumen through the body from the proximal end to the distal end and at least one engaging arm movable between a loaded condition in which the engaging arm is oriented substantially parallel with the sidewall of the body, and a relaxed condition in which the engaging arm is oriented transversely to the sidewall of the body and at least partially disposed within the lumen.

In some examples, the suture clip further includes at least one finger disposed at the distal end of the body; and/or the finger has a loaded condition in which the finger is oriented substantially parallel with the sidewall of the body, and a relaxed condition in which the finger extends radially outward from the body; and/or the finger has a relaxed condition in which the finger forms an angle of between about 0 degrees and about 90 degrees with respect to a longitudinal axis of the body; and/or the at least one finger comprises four fingers evenly distributed about a circumference of the distal end of the body; and/or the at least one engaging arm includes multiple engaging arms, and the at least one finger includes multiple fingers, each of the engaging arms and each of the fingers including at least one slot defined therein; and/or the body is generally cylindrical; and/or the at least one engaging arm comprises two engaging arms disposed on contralateral sides of the body; and/or the two engaging arms are spaced from one another in a length direction of the body; and/or in the relaxed condition, the engaging arm extends at an angle of between about 30 degrees and about 60 degrees with respect to a longitudinal axis of the body; and/or the lumen is sized to receive at least one end of a suture; and/or the lumen is sized to receive multiple strands of a suture; and/or the distal end of the body is blunted; and/or the engaging arm is configured to press a portion of a suture against an inner sidewall of the body in the relaxed condition.

In some embodiments, a system for deploying a suture clip at a target site, the system includes a delivery device including (i) a hollow shaft having a trailing end, a leading end, and a lumen extending therethrough from the trailing end to the leading end, (b) a pusher slidably disposed on the hollow shaft, and (c) a sheath disposed over the hollow shaft and the pusher, and a suture clip disposed on the hollow shaft and within the sheath.

In some examples, the system further includes a slot extending through the sheath in a length direction of the sheath, and an actuator coupled to the pusher and extending through the slot for operation by a user; and/or the suture clip comprises a body having a proximal end, a distal end, and a sidewall defining a lumen through the body from the proximal end to the distal end, and at least one engaging arm movable between a loaded condition in which the engaging arm is oriented substantially parallel with the sidewall of the body, and a relaxed condition in which the engaging arm is oriented transversely to the sidewall of the body and at least partially disposed within the lumen, and wherein the hollow shaft prevents the at least one engaging arm of the suture clip from returning to a relaxed condition; and/or the suture clip further comprises at least one finger disposed at the distal end of the body, and wherein the sheath prevents the at least one finger of the suture clip from returning to a relaxed condition; and/or the pusher has an outer diameter that is approximately equal to an outer diameter of the suture clip in the loaded condition; and/or the system further includes a plurality of suture clips disposed on the hollow shaft and within the sheath.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A suture clip, comprising:
 a body having a proximal end, a distal end, and a sidewall defining a lumen through the body from the proximal end to the distal end, the body including a rib pivotable relative to the sidewall;
 at least one engaging arm attached to the rib and movable between a loaded condition in which the at least one engaging arm is oriented substantially parallel with the sidewall of the body, and a relaxed condition in which the at least one engaging arm is oriented transversely to the sidewall of the body and at least partially disposed within the lumen; and
 at least one finger attached to the rib and movable between a loaded condition in which the at least one finger is oriented substantially parallel with the sidewall of the body, and a relaxed condition in which the at least one finger extends radially outward from the body, whereby pivoting the rib relative to the sidewall moves the at least one engaging arm between the loaded condition and the relaxed condition and moves the at least one finger between the loaded condition and the relaxed condition.

2. The suture clip of claim 1, wherein, in the relaxed condition of the at least one finger, the at least one finger forms an angle of between about 0 degrees and about 90 degrees with respect to a longitudinal axis of the body.

3. The suture clip of claim 1, wherein the at least one finger comprises four fingers evenly distributed about a circumference of the body.

4. The suture clip of claim 1, wherein the at least one engaging arm comprises a plurality of engaging arms, and the at least one finger comprises a plurality of fingers, each of the fingers including at least one slot defined therein.

5. The suture clip of claim 1, wherein the body is generally cylindrical.

6. The suture clip of claim 1, wherein the at least one engaging arm comprises two engaging arms disposed on contralateral sides of the body.

7. The suture clip of claim 6, wherein the two engaging arms are spaced from one another in a direction along a longitudinal axis of the body.

8. The suture clip of claim 1, wherein, in the relaxed condition of the at least one engaging arm, the at least one engaging arm extends at an angle of between about 30 degrees and about 60 degrees with respect to a longitudinal axis of the body.

9. The suture clip of claim 1, wherein the lumen is sized to receive at least one end of a suture.

10. The suture clip of claim 1, wherein the lumen is sized to receive multiple suture strands.

11. The suture clip of claim 1, wherein the body is blunted.

12. The suture clip of claim 1, wherein the at least one engaging arm is configured to press a portion of a suture against an interior surface of the sidewall of the body in the relaxed condition of the at least one engaging arm.

\* \* \* \* \*